US011221251B2

(12) United States Patent
Dinges et al.

(10) Patent No.: US 11,221,251 B2
(45) Date of Patent: Jan. 11, 2022

(54) METHOD AND DEVICE FOR CALIBRATING A LIGHT SOURCE OF A MEDICAL DEVICE

(71) Applicant: Omicron-Laserage Laserprodukte GmbH, Rodgau-Dudenhofen (DE)

(72) Inventors: Dieter Dinges, Oberursel (DE); Wolfgang Fürstenberg, Johannesberg (DE); Sönke-Nils Baumann, Aschaffenburg (DE)

(73) Assignee: OMICRON-LASERAGE LASERPRODUKTE GMBH, Rodgau-Dudenhofe (DE)

( * ) Notice: Subject to any disclaimer, the term of this patent is extended or adjusted under 35 U.S.C. 154(b) by 0 days.

(21) Appl. No.: 16/619,634

(22) PCT Filed: Apr. 18, 2018

(86) PCT No.: PCT/EP2018/059878
§ 371 (c)(1),
(2) Date: Dec. 5, 2019

(87) PCT Pub. No.: WO2018/224211
PCT Pub. Date: Dec. 13, 2018

(65) Prior Publication Data
US 2020/0141797 A1    May 7, 2020

(30) Foreign Application Priority Data
Jun. 7, 2017 (DE) .................. 10 2017 112 483.7

(51) Int. Cl.
*G01J 1/42* (2006.01)
*A61N 5/06* (2006.01)

(52) U.S. Cl.
CPC ............ *G01J 1/4257* (2013.01); *A61N 5/062* (2013.01); *A61N 2005/063* (2013.01); *G01J 2001/4247* (2013.01)

(58) Field of Classification Search
CPC .......................... A61B 1/00057; G01J 1/4257
See application file for complete search history.

(56) References Cited

U.S. PATENT DOCUMENTS 4,800,877 A    1/1989 Losch
5,115,126 A    5/1992 Ams et al.
(Continued)

FOREIGN PATENT DOCUMENTS

WO    2004/105199 A2    12/2004
WO    2018224211 A1    12/2018

OTHER PUBLICATIONS

German Patent Office, Office Action for German Patent Application No. 10 2017 112 483.7, dated Jan. 16, 2018. 6 pages.
(Continued)

*Primary Examiner* — Tony Ko
(74) *Attorney, Agent, or Firm* — SoCal IP Law Group LLP; Guy Cumberbatch

(57) ABSTRACT

The invention relates to a method for calibrating a light source (104) of a medical device (102), wherein the light source (104) is connectable to at least one light-guiding fiber (112) such that electromagnetic radiation of a defined light power that is generated by the light source (104) is at least partly coupled into the light-guiding fiber (112). The medical device (102) is connected to at least one calibration port (108), wherein the calibration port (108) comprises sensor means for determining a spatial emission characteristic of a light-guiding fiber (112) introduced into the calibration port (108). In this case, the method avoids an improper treatment on account of an incorrectly chosen coupled-out intensity of the electromagnetic radiation used.

13 Claims, 3 Drawing Sheets

(56) References Cited

U.S. PATENT DOCUMENTS

| | | |
|---|---|---|
| 10,602,914 B2 * | 3/2020 | Beck .................. G01N 21/6456 |
| 2003/0107726 A1 | 6/2003 | Hirt et al. |
| 2013/0102861 A1 | 4/2013 | Oki et al. |

OTHER PUBLICATIONS

European Patent Office, International Search Report and Written Opinion for PCT Application No. PCT/EP2018/059878, dated Jul. 17, 2018.

Granjon, Y. et al., "Automatic measurement of emitting profile of diffusing top on a medical laser instrument," Medical & Biological Engineering and Computing, May 1994. pp. 323-327.

* cited by examiner

METHOD AND DEVICE FOR CALIBRATING A LIGHT SOURCE OF A MEDICAL DEVICE

RELATED APPLICATION INFORMATION

This patent claims priority from International PCT Patent Application No. PCT/EP2018/059878, filed Apr. 18, 2018 entitled, "METHOD AND DEVICE FOR CALIBRATING A LIGHT SOURCE OF A MEDICAL DEVICE", which claims priority to German Patent Application No. 10 2017 112 483.7, filed Jun. 7, 2017 all of which are incorporated herein by reference in their entirety.

FIELD OF THE INVENTION

The invention relates to a medical device having at least one light source connectable to at least one light-guiding fiber, and a method for calibrating a light source of such a medical device.

BACKGROUND OF THE INVENTION

Diverse applications of laser systems in the medical field are known nowadays in the prior art. Besides the customary applications, such as in surgery or in ophthalmology, for example, the radiation generated by laser systems is increasingly also being used in cancer therapy, for example in the context of photodynamic therapy (PDT). This involves the use of a photosensitive medicament which, as a result of activation with light having a specific wavelength, on account of photophysical processes, releases active substances which attack tumor cells or bacteria, for example. In this case, light having a specific wavelength and a specific intensity (irradiance) is required for activating corresponding medicaments. For this purpose, it is possible to use both laser light and other electromagnetic radiation having a sufficiently narrow spectral bandwidth.

In the case of the treatment options of photodynamic therapy, generally a distinction is drawn between superficial treatment and invasive (in particular interstitial) treatment. In both areas, however, usually the electromagnetic radiation used for the treatment is coupled into a light-guiding fiber and coupled out of the light-guiding fiber at the treatment site. Depending on the type of treatment, the fibers used differ here in their emission properties.

In order to ensure that, during a treatment, the treated tissue is actually exposed to light of the required intensity, it is known in the prior art to calibrate a light source prior to treatment. In this case, in general, the calibration involves comparing whether the entire light power coupled out of a fiber corresponds to the power coupled into the fiber to an extent such that the desired light power is available at the treatment site. If this is not case, the light power coupled into the light-guiding fiber can be adapted such that the light power coupled out corresponds to the medical requirements. However, in general no distinction is drawn regarding the kind of fiber from which light is coupled out and the manner in which light is coupled out from the fiber. In this regard, depending on the design of the fiber, for the same light power coupled out, different intensities coupled out of the fiber can occur. Consequently, in the prior art, there is the risk that although the power coupled out of a fiber in total is correct after a calibration, the intensity is too high or too low on account of an incorrectly chosen fiber, with the result that a treatment is not possible, or injury of the patient is to be feared.

SUMMARY OF THE INVENTION

Against this background, the present invention is based on the object of providing a method for calibrating a light source of a medical device in which an improper treatment on account of an incorrectly chosen coupled-out intensity of the electromagnetic radiation used is avoided.

Main features of the invention are specified in claim 1 and in alternative independent claim 9. Embodiments are the subject matter of claims 2 to 8 and 10.

In a first aspect, the invention relates to a method for calibrating a light source of a medical device, wherein the light source is connectable to at least one light-guiding fiber such that electromagnetic radiation of a defined light power that is generated by the light source is at least partly coupled into the light-guiding fiber. The medical device is connected to at least one calibration port, wherein the calibration port comprises sensor means for determining a spatial emission characteristic of a light-guiding fiber introduced into the calibration port. In this case, the method comprises the following steps.

Firstly, the light-guiding fiber is connected to the light source and a positioning device for the light-guiding fiber is inserted into the calibration port, wherein the positioning device comprises a receiving channel for receiving the light-guiding fiber and also at least one emission opening, wherein the at least one emission opening enables the transmission of a light power coupled out of the light-guiding fiber in at least one defined spatial direction. Afterward, the light-guiding fiber is introduced into the receiving channel of the positioning device and electromagnetic radiation having a defined light power is coupled into the light-guiding fiber. This is followed by determining the spatial emission characteristic of the light power coupled out of the light-guiding fiber in the region of the calibration port by means of the sensor means as an actual emission characteristic and also a desired emission characteristic of the light power coupled out of the light-guiding fiber in the region of the calibration port for the light power coupled into the light-guiding fiber. The determined actual emission characteristic is then compared with the desired emission characteristic, and if the actual emission characteristic corresponds to the desired emission characteristic, the light-guiding fiber is released for further use. By contrast, if the actual emission characteristic does not correspond to the desired emission characteristic, the method ends with outputting an error message.

In one embodiment, the method comprises connecting the light-guiding fiber (112) to the light source (104), inserting a positioning device (110) for the light-guiding fiber (112) into the calibration port (108), wherein the positioning device (110) comprises a receiving channel for receiving the light-guiding fiber (112) and also at least one emission opening, wherein the at least one emission opening enables the transmission of a light power coupled out of the light-guiding fiber (112) in at least one defined spatial direction, introducing the light-guiding fiber (112) into the receiving channel of the positioning device (110), coupling electromagnetic radiation of a defined light power into the light-guiding fiber (112), determining the spatial emission characteristic of the light power coupled out of the light-guiding fiber (112) in the region of the calibration port (108) as an actual emission characteristic, determining a desired emission characteristic of the light power coupled out of the light-guiding fiber (112) in the region of the calibration port (108) for the light power coupled into the light-guiding fiber (112) by means of the sensor means, and comparing the determined actual emission characteristic with the determined desired emission characteristic. If the actual emission characteristic corresponds to the desired emission characteristic, the method furthermore comprises releasing the light-guiding fiber (112) for further use, and if the actual emission characteristic does not correspond to the desired emission characteristic, outputting an error message.

In this case, a "light source" can be any desired source of electromagnetic radiation having a sufficiently narrow spectral bandwidth, such that it is suitable for use in PDT. This can involve for example LEDs, in particular laser diodes for generating laser radiation. In this case, the radiation generated by the light source is preferably coupled by means of a corresponding optical unit into a light-guiding fiber, for example an optical fiber, which can have for example a diameter of 400 µm to 600 µm. Preferably, laser light is used as electromagnetic radiation in the context of the method described.

An emission characteristic in this context describes the ratios of light powers that are emitted from the light-guiding fiber in different spatial directions, taking account of a light power coupled into the light-guiding fiber. In this case, the correspondence of the actual emission characteristic to the desired emission characteristic can be determined taking account of a defined tolerance. By way of example, it is possible to refer to "correspondence" of the characteristics if the respective ratios deviate from one another by less than 5%. In this case, the tolerance level can be chosen differently for different ratios.

In this case, the method described above has the advantage that, rather than the absolute light power coupled out of a light-guiding fiber, the emission characteristic of the radiation coupled out of the light-guiding fiber is used for calibrating the light source. Specifically, what kind of light-guiding fiber is currently connected to the light source can be derived from the emission characteristic of the determined radiation. If the desired emission characteristic is known here for a specific treatment method or kind of fiber, the fact of whether the correct fiber is connected to the light source can be identified by a comparison of the characteristics.

In this case, if the desired emission characteristic does not correspond to the actual emission characteristic, this may have a number of causes. Either the incorrect fiber or the incorrect fiber type is connected to the light source, or the positioning device inserted in the calibration port does not match the light-guiding fiber used since the spatial directions released by the positioning device do not coincide with the emission characteristic of the light-guiding fiber. It is only with use of the correct fiber in combination with the correct positioning device that the actual emission characteristic will correspond to the desired emission characteristic, such that the fiber can be released for a further use.

A "further use" can be, for example, the adaptation of the light power coupled into the light-guiding fiber, such that a treatment can be started on account of a sufficient intensity coupled out of the light-guiding fiber. If the light power coupled out of the light-guiding fiber is already sufficient for a treatment, as further use the treatment of a patient can also be started directly.

The error message output in the case where an actual emission characteristic does not correspond to the desired emission characteristic can here contain information as to what error source is presumably present. In this regard, on the basis of the deviations, it is possible to determine for example whether the incorrect fiber or the incorrect positioning device was used. In this case, the desired emission characteristic used for the comparison of the characteristics can for example be read out from a memory of the medical device and be defined on the basis of information regarding the light-guiding fiber used.

In the event of an error message being output, according to one embodiment provision can be made for the medical device automatically to be put into a safe state in which a further emission of electromagnetic radiation by the light sources is prevented. In this case, provision can be made for said safe state to be canceled again only if a change of the present configuration of the medical device is effected. Such a change can be for example an exchange of the light-guiding fiber or the positioning device, or a change of the light power coupled into the light-guiding fiber. In this case, the error message can contain an indication that the device can be reactivated only after such a change of the configuration.

In this case, insofar as logically meaningful, the individual method steps of the method according to the invention can also be carried out in a different order. In this regard, by way of example, inserting the positioning device into the calibration port can indeed also be carried out before connecting the light-guiding fiber to the light source. Equally, a desired emission characteristic can also be determined before the actual emission characteristic is known.

As has already been explained above, the light-guiding fibers used can differ in their emission characteristic. In this case, according to one embodiment provision is made for a light-guiding fiber to be a fiber of a first fiber type or of a second fiber type, wherein the first fiber type is configured to emit electromagnetic radiation coupled into the light-guiding fiber in the longitudinal direction of the fiber, and wherein the second fiber type is configured to emit electromagnetic radiation coupled into the light-guiding fiber transversely with respect to the longitudinal direction of the fiber over a defined length of the fiber. In this case, the method furthermore comprises determining the fiber type used, wherein the determination of the desired emission characteristic takes account of the determined fiber type.

In the case of the second fiber type, it can be provided here that, when determining the fiber type, the length of the fiber over which electromagnetic radiation is coupled out of the fiber in a radial direction is simultaneously determined as well. Furthermore, further fiber parameters can also be encoded in information regarding a fiber type. By way of example, when determining a first fiber type, information regarding the shape of the fiber cross-section can simultaneously be obtained.

In order to determine the fiber type, provision can be made for example for the fiber to be equipped with an RFID chip or a similar identification feature from which the fiber type can be derived. In this case, by way of example, at the moment when the fiber is connected to the light source, the medical device, by reading from the RFID chip, can independently determine what fiber type was connected, and accordingly select the desired emission characteristic to be expected. This has the advantage that an error source, namely an erroneous operation of the device in the sense of an erroneous selection of the connected fiber, can be avoided.

As an alternative to an automatic identification of the fiber type, according to a further embodiment provision is made for determining the fiber type used to comprise a user input. In order to further simplify the calibration of a light source of a medical device, according to a further embodiment provision is made for the method furthermore to include determining the defined light power to be coupled into the light-guiding fiber on the basis of the fiber type connected to the light source. In this case, by way of example, provision can be made for a user or the medical device itself to predefine an intensity to be coupled out of the light-guiding fiber, which intensity is automatically converted into a light power to be coupled into the fiber by the medical device on the basis of information about the light-guiding fiber to be used. As a result, the probability of an incorrect operation is reduced further.

According to a further embodiment it is also possible for a user to predefine only a specific kind of therapy and the size of an area to be treated, whereupon the medical device independently determines what fiber type must be used and what light power ought to be coupled into the fiber in order to be able to couple the intensity required for the treatment out of the fiber. Accordingly, the medical device also determines from the selected kind of therapy what desired emission characteristic is to be expected. Consequently, the definition of the therapy parameters can be completely automated, with the result that an incorrect operation is virtually precluded.

According to a further embodiment, the sensor means comprise at least one lateral photodiode arranged laterally at the calibration port, and also at least one frontal photodiode arranged at a longitudinal end of the calibration port. In this case, determining the actual emission characteristic comprises determining the respective photocurrent generated in the photodiodes by the light power coupled out from the light-guiding fiber, wherein comparing the determined actual emission characteristic with the determined desired emission characteristic comprises comparing the determined photocurrents with photocurrents contained in the desired emission characteristic for the respective photodiodes.

The use of at least one lateral photodiode and one frontal photodiode allows, on the basis of the determined photocurrents, a dedicated comparison of the emission longitudinally and transversally with respect to a light-guiding fiber used. Preferably, two lateral photodiodes are provided here, which are situated diametrically opposite one another in the calibration port. A better resolution of the emission characteristic of the light-guiding fiber is possible as a result of such an arrangement. In this case, it is possible to consider the photodiodes or the photocurrents generated in the photodiodes for determining an emission characteristic both in combination and separately. Depending on the number of photodiodes used, arbitrary combinations of photocurrents of differently positioned photodiodes can also influence the determination of the emission characteristic.

With the use of the photocurrents for determining the desired and actual emission characteristics, according to a further embodiment it is provided that if the ratios of the photocurrents of the actual emission characteristic correspond to the ratios of the photocurrents of the desired emission characteristic, but the photocurrents of the actual emission characteristic are lower than the corresponding photocurrents of the desired emission characteristic, the error message indicates a defect of the light-guiding fiber and/or of the coupling between the light-guiding fiber and the light source. Specifically, if the actual emission characteristic per se, which describes the ratios of determined light powers as described above, corresponds to the desired emission characteristic, the light-guiding fiber used in combination with the positioning device used has been chosen correctly. However, if the absolute values of the photocurrents overall are too low, this indicates an increased loss of light power in the fiber or in the region between light source and light-guiding fiber. This is the case in particular if the medical device is configured independently to choose the light power to be coupled into the light-guiding fiber on the basis of a choice of a desired therapy variant by a user.

It has been described above that the medical device comprises one light source, which can be connected to at least one light-guiding fiber and then be calibrated in accordance with the method according to the invention. According to a further embodiment, provision is made here for the medical device to comprise at least two light sources, which are in each case connectable to a light-guiding fiber such that electromagnetic radiation generated by the light sources is in each case at least partly coupled into the light-guiding fiber connected to a light source. In this case, the method steps are carried out individually for the light-guiding fibers connected to the light sources, wherein inserting a positioning device need not necessarily be carried out for each light-guiding fiber. In this regard, it is indeed possible for identical fibers to be used at different light sources, such that it is not necessary to exchange the positioning device between the calibration processes. By contrast, if the light-guiding fibers connected to the individual light sources differ in their emission characteristic on account of different emission directions (frontal or radial), the corresponding positioning device inserted in the calibration port must also be exchanged when carrying out the calibration process. In this way, a multiplicity of light-guiding fibers can be calibrated in parallel, thereby enabling a treatment in a plurality of regions of a patient to be treated in parallel.

In order to further simplify the operation of the medical device or the implementation of the calibration method, according to a further embodiment it is provided that after the release of a fiber, the light source connected to the fiber couples light having a wavelength of between 350 nm and 850 nm into the fiber for a defined time period. Effectively an already calibrated light-guiding fiber then continues to be luminous for a time period, for example 5 minutes, in the electromagnetic spectrum visible to human beings, and so a user can easily recognize which fibers have already been calibrated and which have not yet been calibrated. A further advantage of this embodiment is that after a calibration has been carried out, the sensor means of the calibration port still detect radiation if the calibrated fiber has not been removed from the calibration port. In this case, it is possible to display to a user an error message that the incorrect fiber is arranged in the calibration port or the calibration of the fibers has already been concluded. In this way, a mix-up of the fibers between fibers that have already been calibrated and fibers that have not yet been calibrated can accordingly be avoided.

In order to increase the safety of the method for a user, according to a further embodiment it is provided that, upon identification of a momentary change in the measured emission characteristic during the calibration process, the medical device switches into a safe state in which for example the at least one light source of the medical device is switched off and is initially no longer activatable by a user. Such a momentary change in the measured emission characteristic occurs for example if the light-guiding fiber is withdrawn from the calibration port in the interim, or is severed at a position along the fiber. Switching off the light sources makes it possible to prevent the electromagnetic radiation that emerges from the light-guiding fiber from resulting in injuries to a user. The safe state of the medical device can be canceled again for example by a corresponding user input.

In a further aspect, the invention relates to a medical device comprising at least one light source, wherein the light source is connectable to at least one light-guiding fiber such that electromagnetic radiation of a defined light power that is generated by the light source is at least partly coupled into the light-guiding fiber. The medical device is connected to at least one calibration port, wherein the calibration port comprises sensor means for determining a spatial emission characteristic of a light-guiding fiber introduced into the calibration port, and wherein the device is configured to couple electromagnetic radiation of a defined light power into a light-guiding fiber connected to the device and positioned in the calibration port, to determine the spatial emission characteristic of the light power coupled out of the light-guiding fiber in the region of the calibration port as an actual emission characteristic, to determine a desired emission characteristic of the light power coupled out of the light-guiding fiber in the region of the calibration port for the light power coupled into the light-guiding fiber, to compare the determined actual emission characteristic with the determined desired emission characteristic and if the actual emission characteristic corresponds to the desired emission characteristic, to release the light-guiding fiber for use. If the actual emission characteristic does not correspond to the desired emission characteristic, the device is furthermore configured to output an error message.

In this case, according to one embodiment provision is made for the sensor means to comprise at least one lateral photodiode arranged laterally at the calibration port, and also at least one frontal photodiode arranged at the longitudinal end of the calibration port. The device is then configured, for determining the actual emission characteristic, to determine the respective photocurrent generated in the photodiodes by the light power coupled out from the light-guiding fiber, and is furthermore configured, for comparing the determined actual emission characteristic with the determined desired emission characteristic, to compare the determined photocurrents with photocurrents contained in the desired emission characteristic for the respective photodiodes.

BRIEF DESCRIPTION OF THE DRAWINGS

Further features, details and advantages of the invention are evident from the wording of the claims and also from the following description of exemplary embodiments with reference to the drawings, in which:

In the text hereinafter, features that are similar or identical to one another are identified by the same reference signs.

DETAILED DESCRIPTION OF THE INVENTION

Figure 1:
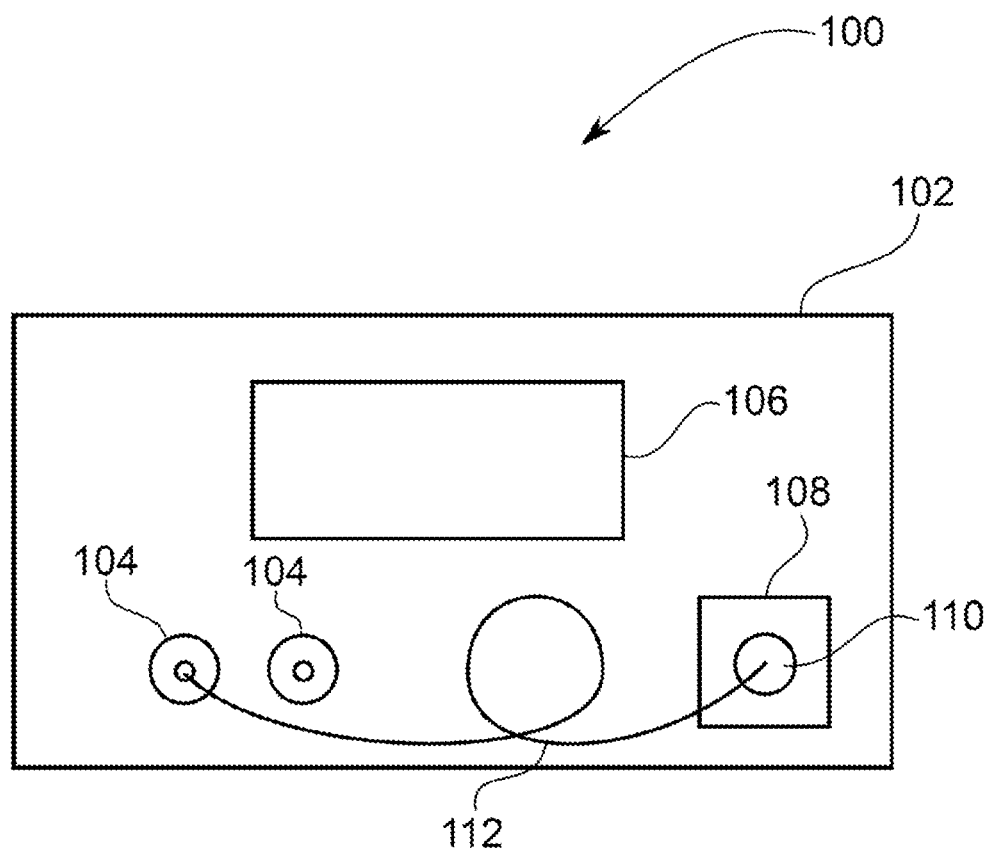
FIG. 1 shows a schematic illustration of system for carrying out the method according to the invention.

FIG. 1 shows a schematic illustration of a system 100 suitable for carrying out the method according to the invention. For this purpose, the system 100 comprises a medical device 102, which in the illustrated embodiment has two light sources 104, an operating element 106 and a calibration port 108. The operating element 106 can be a touch-sensitive display, for example, which is suitable both for displaying operation parameters and for the setting of desired operation parameters by a user of the system 100. Although the operating element 106 is illustrated as an integral element in FIG. 1, provision can also be made for the operating element 106 to consist of a plurality of elements. By way of example, in addition to the operating element 106, provision can also be made of an emergency off switch on the medical device 102, which enables the light sources 104 to be switched off for a short period.

The system 100 further comprises a positioning device 110, which is inserted into the calibration port 108, and also, in the embodiment illustrated, a light-guiding fiber 112, which firstly at one end is connected to a light source 104 and secondly is inserted by the other end of the light-guiding fiber 112 into the positioning device 110. In this case, the light-guiding fiber 112 can be connected to the light sources 104 for example via corresponding fiber connectors, for example via FC/PC or F-SMA connectors or a proprietary plug connection. The system 100 can be used in the context of photodynamic therapy, for example, as has already been mentioned in the introduction. In this case, firstly a medicament comprising a photoactivatable substance is administered to a patient. If said substance is irradiated with light having a specific wavelength and intensity, a conversion or activation of an active ingredient of the substance takes place on account of photophysical processes, with the result that for example bacteria or cancer cells are attacked by the active ingredient. Depending on the kind of treatment, in this case different kinds of light-guiding fibers 112 and different intensities are introduced into the tissue to be treated. For this purpose, it is generally necessary for the light power coupled into the light-guiding fiber 112 by the light sources 104 to be coordinated with the kind of light-guiding fiber 112 and also with the area to be treated. In this case, with regard to the kind of light-guiding fibers 112, a distinction is usually drawn between frontally emissive light-guiding fibers 112 and radially emissive light-guiding fibers 112, wherein the emission is effected over a defined length of the fiber in the case of the radially emissive fibers.

If, with the use of a radially emissive fiber 112, for example, a specific light power is chosen for a specific length of the emissive region of the fiber 112, but a fiber 112 having an emissive length different therefrom is inserted, this results in an intensity deviating from the actual desired parameters, which intensity is coupled out of the light-guiding fiber 112 during a treatment. As a result, either the medicament cannot be activated or there is the risk of burns in the treated tissue on account of an excessively high light power. According to the invention, such an incorrect treatment is intended to be avoided by virtue of the light-guiding fiber 112 connected to the light source 104 firstly being calibrated by means of the calibration port 108 before release for a treatment.

Figure 2:
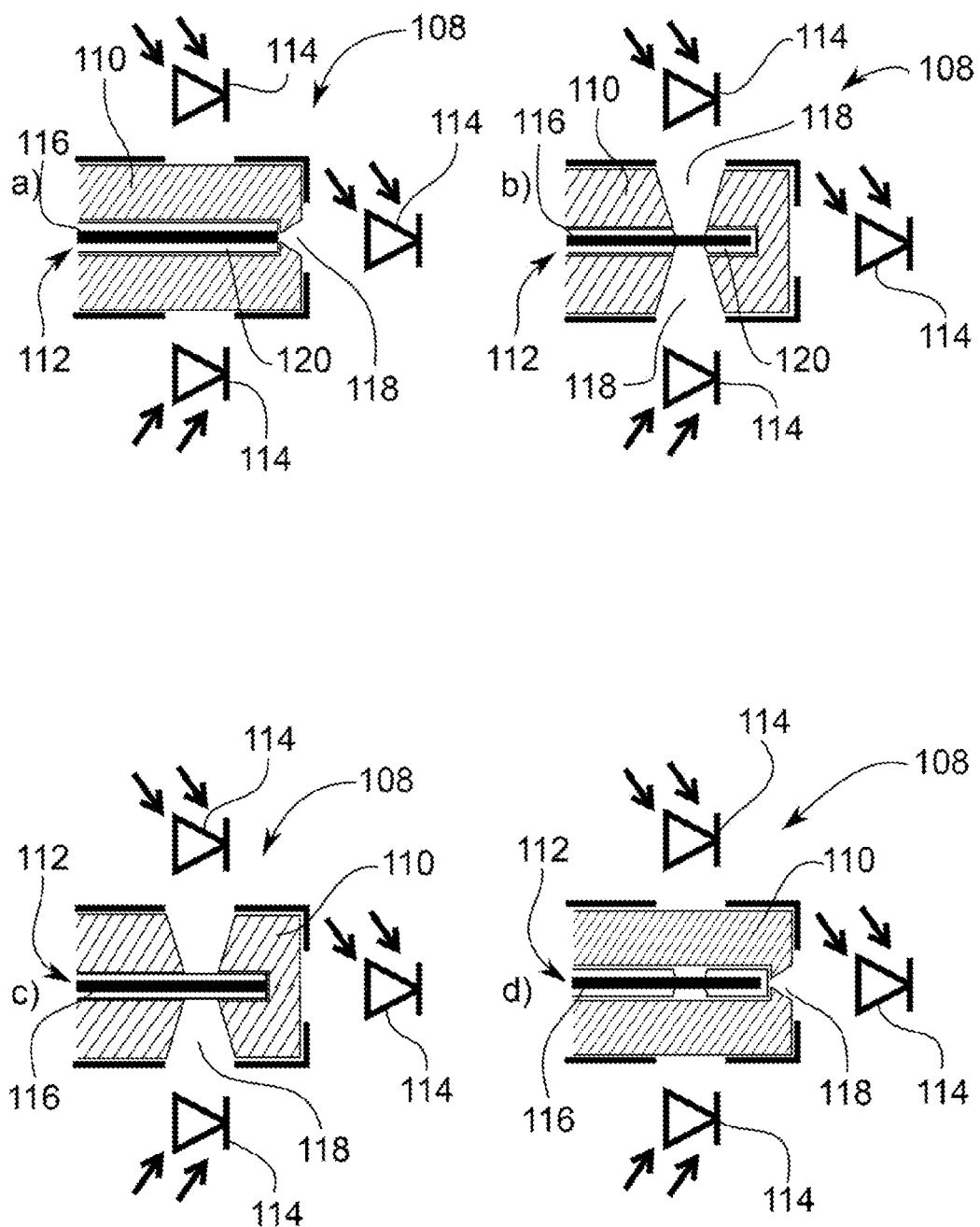
FIG. 2 shows schematic illustrations of a calibration port with a positioning device and a fiber.

FIG. 2 illustrates various possible configurations of calibration ports 108 with positioning devices 110 and light-guiding fibers 112 inserted therein, which can occur in the course of a calibration of a light-guiding fiber 112. In all of the variants illustrated, the calibration port 108 comprises three photodiodes 114, which are arranged in the calibration port 108 such that they can detect electromagnetic radiation emitted within the calibration port 108 and can quantify it on the basis of a photocurrent generated in the photodiodes as a result.

The calibration port 108 is preferably a circular, e.g. cylindrically shaped, cutout, into which a correspondingly shaped positioning device 110 can be inserted. The positioning device 110 is for example a body which is produced from plastic and which has the effect of being absorbent at least partly for the electromagnetic radiation emerging from the light-guiding fiber 112. By way of example, the positioning device 110 can be produced from polyoxymethylene (POM). Various combinations of fiber types and positioning devices 110 are illustrated in FIGS. 2a), 2b), 2c) and 2d).

FIG. 2a) illustrates a light-guiding fiber 112 which, at its fiber end, is configured to couple out the electromagnetic radiation guided in the light-guiding fiber 112 or in the core 120 of the light-guiding fiber 116 in a frontal direction of fiber 112. The positioning device 110 arranged in the calibration port 108 in FIG. 2a) is adapted here to this kind of light-guiding fiber 112. For this purpose, the positioning device 110, which is preferably embodied as a rotationally symmetrical body, has a cutout 118 at its end face, through which cutout electromagnetic radiation coupled out of the light-guiding fiber 112 or the fiber core 116 can emerge from the positioning device 110.

In order to ascertain the emission characteristic of the combination of positioning device 110 and light-guiding fiber 112, the photocurrents generated in the photodiodes 114 on account of the electromagnetic radiation emerging from the calibration port 108 are measured. On account of the kind of light-guiding fiber 112 and the geometry of the positioning device 110, it should be expected that the photodiode 114 arranged at the longitudinal end of the calibration port 108 will detect a comparatively high photocurrent, while the photodiodes 114 arranged laterally at the calibration port 108 will detect only a comparatively low photocurrent since a large portion of the radiation emerging from the light-guiding fiber 112 in the radial direction is absorbed by the material of the positioning device 110. This corresponds to the emission characteristic to be expected for the correct combination of light-guiding fiber 112 and positioning device 110. In this case, provision is made for the positioning device 110 to be partly transparent to the electromagnetic radiation coupled out of the light-guiding fiber 112, such that the photodiodes 114 arranged at the sides of the calibration port 108 are also exposed to electromagnetic radiation having a low light power on account of scattering within the positioning device 110.

FIG. 2b) shows the situation in which a positioning device 110 for a laterally or radially emissive light-guiding fiber 112 in combination with such a radially emissive light-guiding fiber 112 is inserted in a calibration port 108 identical to that in FIG. 2a). In the case of the light-guiding fiber 112, here the cladding 120 of the light-guiding fiber, which generally completely shields an emission of electromagnetic radiation, is open over a defined region along the length of the fiber 112, such that electromagnetic radiation can emerge from the fiber 112 in a radial direction. In order to make it possible that radiation can emerge from the light-guiding fiber 112 radially, the fiber core 116 can be provided with targeted microdamage as scattering centers configured to scatter incident electromagnetic radiation transversely with respect to the fiber 112. In this case, the scattering centers are preferably distributed uniformly in the entire fiber core 116. Furthermore, the fiber core 116 can be replaced in sections by a diffuser material that scatters incident electromagnetic radiation transversely with respect to the fiber 112. The diffuser material can be for example a silicone with light-scattering particles (flakes) contained therein. In this case, the positioning device 110 is embodied precisely such that it has lateral cutouts 118 which, with a light-guiding fiber 112 introduced completely into the positioning device 110, are arranged precisely in the region of the exposed fiber core 116, such that electromagnetic radiation emerging from the fiber core 116 radially can be detected by the lateral photodiodes 114 of the calibration port 108.

At the longitudinal end of the light-guiding fiber 112, by contrast, the fiber 112 is configured such that no electromagnetic radiation is coupled out of the fiber in the longitudinal direction of the fiber 112. This is illustrated by a closed fiber cladding 120. Preferably, there is arranged at the end of the fiber an element that blocks the electromagnetic radiation, such as a mirror, for example, which has the effect that light power that has not yet been coupled out of the fiber 112 radially is reflected back again into the radially emissive region of the fiber 112. As a result, the residual electromagnetic radiation passes once again through the radially emissive region of the light-guiding fiber 112, with the result that it is possible to achieve a radially coupled-out light power which is higher and more homogeneous over the length of the radially emissive region of the fiber 112.

The emission characteristic to be expected from the combination of positioning device 110 and light-guiding fiber 112 in accordance with FIG. 2a) consists in the fact that the photodiodes 114 arranged laterally in the calibration port 108 will detect a comparatively high photocurrent, while the photodiode 114 arranged frontally in the calibration port 108 will detect only a very low photocurrent.

In the case of a calibration according to the invention, in the case of the combinations as illustrated in FIGS. 2a) and 2b), the determined emission characteristic or actual emission characteristic would in each case correspond to the desired emission characteristic to be expected, provided that a treatment with the corresponding fiber type is actually envisaged. Consequently, in this case, after the calibration, the fiber would be released for a further use since evidently the correct kind of light-guiding fiber 112 is connected to the light source 104.

FIG. 2c) illustrates a combination of a positioning device 110 for a radially emissive fiber 112 with a light-guiding fiber 112 configured for the frontal emission of electromagnetic radiation. If, in this combination, the light-guiding fiber 112 were exposed to electromagnetic radiation having a defined light power, in each case only a very low photocurrent would be detected both by the frontally arranged photodiode 114 of the calibration port 108 and by the laterally arranged photodiodes 114 of the calibration port 108. In a frontal direction the electromagnetic radiation coupled out of the light-guiding fiber 112 would be damped by the positioning device 110, while in a radial direction electromagnetic radiation is prevented from emerging from the light-guiding fiber on account of the continuous fiber cladding 120. Accordingly, the determined actual emission characteristic would not correspond to a desired emission characteristic to be expected for a frontally or radially emissive fiber. Consequently, according to the invention, in the course of the calibration, the light-guiding fiber 112 would not be released for further uses, rather an error message would be output, indicating that either the incorrect light-guiding fiber 112 or the incorrect positioning device 110 was used.

FIG. 2d) illustrates the orthogonal case with respect to FIG. 2c), wherein a radially emissive light-guiding fiber 112 was used in combination with a positioning device 110 provided for the frontal emission of electromagnetic radiation from the light-guiding fiber 112. In this case, too, upon the light-guiding fiber 112 being exposed to electromagnetic radiation, in each case only a very low photocurrent would be detected by all the photodiodes 114 of the calibration port 108 since in a radial direction the emitted radiation is absorbed by the positioning device 110, while in a frontal direction the cladding 120 of the light-guiding fiber 112 would prevent an emission of electromagnetic radiation.

Consequently, here, too, upon a comparison of the determined actual emission characteristic with a desired emission characteristic, a discrepancy between the characteristics would be determined, such that the fiber 112 provided for calibration is not released for a further use, rather an error message is output.

By way of example, if a chosen treatment method or a treatment scenario stipulated that a radially emissive light-guiding fiber 112 is to be used, but the emission characteristic were determined in accordance with FIG. 2a), according to the invention the light-guiding fiber 112 would likewise not be released for a further use. Analogously to this, for an application requiring a frontally emissive light-guiding fiber 112, upon detection of the emission characteristic in accordance with FIG. 2b), the light-guiding fiber 112 would likewise not be released for a further use.

As has already been mentioned above, the length of the emissive region of a radially emissive light-guiding fiber 112 can differ depending on the application scenario. In this case, the positioning device 110 is preferably configured such that it is possible to use a positioning device for different lengths of the radially emissive region of the light-guiding fiber 112. A differentiation of light-guiding fibers 112 having radially emissive regions of different lengths is then possible taking account of the light power coupled into the fiber 112.

By way of example, if provision is made for an input power of 2 watts to be coupled into a light-guiding fiber 112 which couples out electromagnetic radiation in a radial direction over a length of 2 cm, this results in a specific emission characteristic with regard to the ratios of the light powers which are coupled out of the fiber in different spatial directions and which are measured by the photodiodes 114 of the calibration port 108. If, however, in the case of an input power of 2 watts, a fiber which couples out electromagnetic radiation in a radial direction over a length of 4 cm, for example, were mistakenly connected to the light source 104, the intensity emerging from the fiber would not correspond to the expected values for the fiber actually envisaged. Consequently, an error message would be output by the medical device 102.

It is possible, however, that, for a fiber having a shorter or longer radially emissive region, the same ratios of the light powers or intensities coupled out radially are measured by the photodiodes 114 of the calibration port 108. For this purpose, however, in the case of a shorter radially emissive region a lower input power, or in the case of a longer radially emissive region a higher input power, would have to be coupled into the light-guiding fiber 112. Consequently, although the ratios of the light powers coupled out of the fiber possibly do not differ for different fiber types, a differentiation of the fiber types is still possible taking account of the light power coupled into the fiber.

Figure 3:
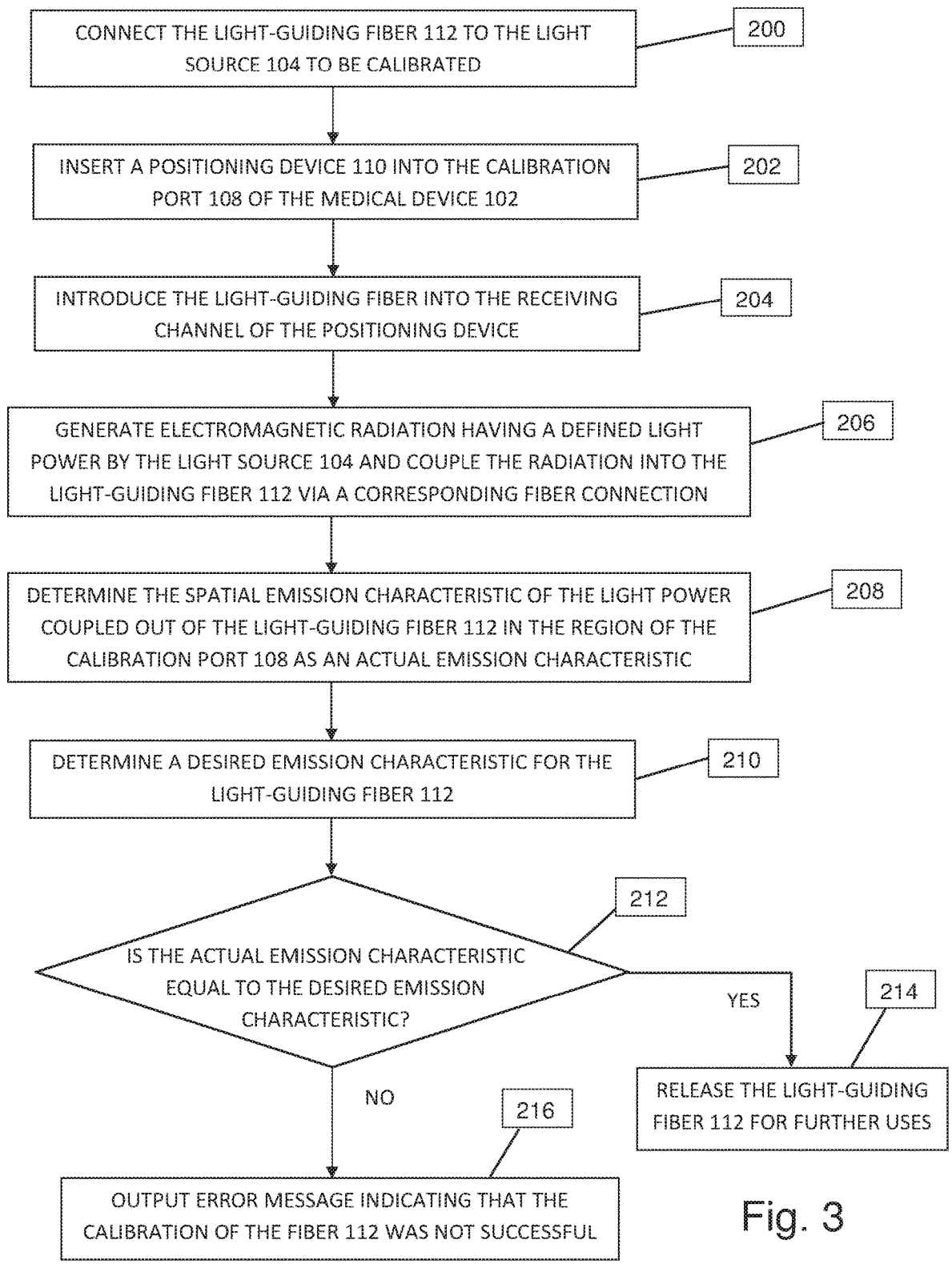
FIG. 3 shows a flow diagram of the method according to the invention.

FIG. 3 illustrates a flow diagram of the method according to the invention for calibrating a light source of a medical device. By way of example, the system 100 as illustrated in FIG. 1 can be used for this purpose. In a first method step 200, firstly the light-guiding fiber 112 is connected to the light source 104 to be calibrated of the medical device 102. Furthermore, a positioning device 110 as illustrated in FIG. 2, for example, in step 202, is inserted into the calibration port 108 of the medical device 102. It should be noted here that the calibration port 108 need not necessarily be embodied in the medical device 102. Rather, the calibration port 108 can also be a separate element connected to the medical device 102 via a corresponding data connection such that it is possible to communicate actual emission characteristics determined by the calibration port 108 to the medical device 102.

After the light-guiding fiber 112 has been connected to the light source 104 and the positioning device 110 has been inserted in the calibration port 108, in method step 204, the light-guiding fiber is introduced into the receiving channel of the positioning device. For this purpose, the positioning device 110 preferably has a funnel-shaped course at a first end side projecting from the calibration port 108, such that the light-guiding fiber 112 can easily be introduced into the channel of the positioning device that is provided for the fiber. In this case, the fiber 112 must be introduced into the positioning device 110 to a stop, such that the respective emissive regions of the light-guiding fiber 112 become located in the corresponding regions or in the region of the cutouts 118 of the positioning device 110. Otherwise, an erroneous emission characteristic would possibly be determined despite a correctly chosen combination of light-guiding fiber 112 and positioning device.

For example in a manner triggered by a corresponding actuation of the medical device 102 by way of the operating elements 106, in step 206, electromagnetic radiation having a defined light power is then generated by the light source 104 and coupled into the light-guiding fiber 112 via a corresponding fiber connection. In this case, the radiation coupled into the light-guiding fiber 112 is coupled out of the corresponding regions of the light-guiding fiber 112 in the region of the calibration port, such that, in method step 208, the spatial emission characteristic of the light power coupled out of the light-guiding fiber 112 in the region of the calibration port 108 can be determined as an actual emission characteristic by means of the photodiodes 114 of the calibration port 108.

Afterward, a desired emission characteristic for the light-guiding fiber 112 is determined in step 210. In this case, by way of example, provision can be made for the medical device 102 to stipulate, on the basis of the indication of a desired kind of treatment, what type of light-guiding fiber 112 is to be connected to the light source 104. In this case, the desired emission characteristic is selected on the basis of the information regarding the fiber type to be used. Alternatively, the light-guiding fiber 112 itself can also be equipped with an identification feature, for example an RFID chip, which is read by a corresponding reader at the connection between light source 104 and light-guiding fiber 112. In this case, the medical device 102 can independently determine what light-guiding fiber 112 or what fiber type was connected to the light source 104.

The desired emission characteristic is then ascertained on the basis of the determined fiber type and can be read out for example from a storage medium kept available in the medical device 102.

In the subsequent method step 212, the determined actual emission characteristic is then compared with the determined desired emission characteristic. If it is determined here that the actual emission characteristic corresponds to the desired emission characteristic, the light-guiding fiber 112 is released for further uses. This is done in method step 214. In this case, the correspondence of the actual emission characteristic to the desired emission characteristic can be determined taking account of a tolerance, such that the desired emission characteristic and the actual emission characteristic need not be identical, but are intended to correspond within certain tolerances. The further use of the light-guiding fiber can be for example the direct treatment of a patient or the light power coupled into the light-guiding fiber can be adapted beforehand such that the intensity coupled out of the light-guiding fiber corresponds to the intensity required for a treatment.

By contrast, if it was determined in step 212 that the actual emission characteristic does not correspond to the desired emission characteristic, that is to say lies outside the tolerances possibly present, an error message is output in step 216, said error message indicating that the calibration of the fiber 112 was not successful. In this case, the error message can for example also indicate that an incorrect fiber type or an incorrect positioning device 110 was used, or that, for a given light power coupled in, the light power emerging from the light-guiding fiber 112 is distinctly too low, which may indicate a defect of the light-guiding fiber 112 or of the fiber input coupling, or is distinctly too high, which may likewise indicate a defect or an incorrectly chosen length of the radially emissive region of a light-guiding fiber 112. In this case, the error message can contain corresponding information.

With the use of a plurality of light-guiding fibers 112, each connected to a light source 104 of the medical device, the method described above can be repeated individually for each of the fibers 112. In this case, according to one embodiment provision can be made for a fiber 112 that has already been released, after the calibration, to continue to emit light in the range of the spectrum visible to human beings, with the result that a user can easily recognize whether or not a fiber 112 has already been calibrated.

The invention is not restricted to one of the embodiments described above, but rather is modifiable in diverse ways.

In this regard, instead of three photodiodes 114, provision can be made of a substantially arbitrary number of photodiodes 114 in a calibration port 108, which can be arranged arbitrarily within the calibration port. In this case, a higher number of photodiodes 114 can result in better or more accurate detection of a spatial emission characteristic of a light-guiding fiber 112.

Furthermore, the photodiodes 114 can also be replaced by other sensor means, such as CCD or CMOS sensors, for example. Use of such sensors would make it possible to determine for example a detailed image of the electromagnetic radiation emerging from the positioning device, and the fiber type which is currently being used in the course of a calibration process can likewise be determined from this image.

It has further been explained above that essentially two kinds of positioning devices 110 are provided, namely those which allow an emission of electromagnetic radiation in a radial direction, or those which allow an emission of electromagnetic radiation in a longitudinal direction. However, in the context of the present invention it is indeed possible to use a positioning device 110 which is suitable for both emission directions simultaneously. The positioning device 110 merely has to be fashioned such that a spatial emission characteristic of a light-guiding fiber 112 arranged in the positioning device can be determined.

All features and advantages, including structural details, spatial arrangements and method steps, which are evident from the claims, the description and the drawing may be essential to the invention both by themselves and in a wide variety of combinations.

LIST REFERENCE SIGNS

100 System
102 Medical device
104 Light source
106 Operating element
108 Calibration port
110 Positioning device
112 Light-guiding fiber
114 Photodiode
116 Fiber core
118 Cutout
120 Fiber cladding

The invention claimed is:

1. A method for calibrating a light source (104) of a medical device (102), wherein the light source (104) is connectable to at least one light-guiding fiber (112) such that electromagnetic radiation of a defined light power that is generated by the light source (104) is at least partly coupled into the light-guiding fiber (112), wherein the medical device (102) is connected to at least one calibration port (108), wherein the calibration port (108) comprises sensor means for determining a spatial emission characteristic of a light-guiding fiber (112) introduced into the calibration port (108), wherein the at least one light-guiding fiber (112) is a fiber (112) of a first fiber type or of a second fiber type, wherein the first fiber type is configured to emit electromagnetic radiation coupled into the light-guiding fiber (112) in the longitudinal direction of the fiber (112), and wherein the second fiber type is configured to emit electromagnetic radiation coupled into the light-guiding fiber (112) transversely with respect to the longitudinal direction of the fiber (112) over a defined length of the fiber (112), wherein the method comprises the following steps:
  a) connecting the light-guiding fiber (112) to the light source (104),
  b) inserting a positioning device (110) for the light-guiding fiber (112) into the calibration port (108), wherein the positioning device (110) comprises a receiving channel for receiving the light-guiding fiber (112) and also at least one emission opening, wherein the at least one emission opening enables the transmission of a light power coupled out of the light-guiding fiber (112) in at least one defined spatial direction,
  c) introducing the light-guiding fiber (112) into the receiving channel of the positioning device (110),
  d) coupling electromagnetic radiation of a defined light power into the light-guiding fiber (112),
  e) determining the fiber type used,
  f) determining the spatial emission characteristic of the light power coupled out of the light-guiding fiber (112) in the region of the calibration port (108) as an actual emission characteristic, wherein the determination of the desired emission characteristic takes account of the determined fiber type,
  g) determining a desired emission characteristic of the light power coupled out of the light-guiding fiber (112) in the region of the calibration port (108) for the light power coupled into the light-guiding fiber (112) by means of the sensor means,
  h) comparing the determined actual emission characteristic with the determined desired emission characteristic,
  i) if the actual emission characteristic corresponds to the desired emission characteristic, releasing the light-guiding fiber (112) for further use, and
  j) if the actual emission characteristic does not correspond to the desired emission characteristic, outputting an error message.

2. The method as claimed in claim 1, wherein determining the fiber type used comprises a user input.

3. The method as claimed in claim 1, wherein the method furthermore includes determining the defined light power to be coupled into the light-guiding fiber (112) on the basis of the fiber type connected to the light source (104).

4. The method as claimed in claim 1, wherein the sensor means comprise at least one lateral photodiode (114) arranged laterally at the calibration port (108), and also at least one frontal photodiode (114) arranged at a longitudinal end of the calibration port (108), wherein determining the actual emission characteristic comprises determining the respective photocurrent generated in the photodiodes (114) by the light power coupled out from the light-guiding fiber (112), and wherein comparing the determined actual emission characteristic with the determined desired emission characteristic comprises comparing the determined photocurrents with photocurrents contained in the desired emission characteristic for the respective photodiodes (114).

5. The method as claimed in claim 4, wherein if the ratios of the photocurrents of the actual emission characteristic correspond to the ratios of the photocurrents of the desired emission characteristic, but the photocurrents of the actual emission characteristic are lower than the corresponding photocurrents of the desired emission characteristic, the error message indicates a defect of the light-guiding fiber (112) and/or of the coupling between the light-guiding fiber (112) and the light source (104) and/or a defective emissive area of the light-guiding fiber (112).

6. The method as claimed in claim 1, wherein the medical device (102) comprises at least two light sources (104), which are in each case connectable to a light-guiding fiber (112) such that electromagnetic radiation generated by the light sources (104) is in each case at least partly coupled into the light-guiding fiber (112) connected to a light source (104), wherein at least method steps a) and c) to i) are carried out individually for the light-guiding fibers (112) connected to the light sources (104).

7. The method as claimed in claim 1, wherein after the step of releasing the light-guiding fiber (112) release of a fiber (112), the light source (104) connected to the fiber (112) couples light having a wavelength of between 350 nm and 850 nm into the fiber (112) for a defined time period.

8. A medical device (102) comprising at least one light source (104), wherein the light source (104) is connectable to at least one light-guiding fiber (112) such that electromagnetic radiation of a defined light power that is generated by the light source (104) is at least partly coupled into the light-guiding fiber (112), wherein the medical device (102) is connected to at least one calibration port (108), wherein the calibration port (108) comprises sensor means for determining a spatial emission characteristic of a light-guiding fiber (112) introduced into the calibration port (108), wherein the sensor means comprise at least one lateral photodiode (114) arranged laterally at the calibration port (108), and also at least one frontal photodiode (114) arranged at a longitudinal end of the calibration port (108), wherein the device (102) is configured:

to couple electromagnetic radiation of a defined light power into a light-guiding fiber (112) connected to the device (102) and positioned in the calibration port (108), to determine the spatial emission characteristic of the light power coupled out of the light-guiding fiber (112) in the region of the calibration port (108) as an actual emission characteristic, wherein the device (102) for determining the actual emission characteristic is configured to determine the respective photocurrent generated in the photodiodes (114) by the light power coupled out from the light-guiding fiber (112), to determine a desired emission characteristic of the light power coupled out of the light-guiding fiber (112) in the region of the calibration port (108) for the light power coupled into the light-guiding fiber (112), to compare the determined actual emission characteristic with the determined desired emission characteristic, wherein the device (102) for comparing the determined actual emission characteristic with the determined desired emission characteristic is configured to compare the determined photocurrents with photocurrents contained in the desired emission characteristic for the respective photodiodes (114), if the actual emission characteristic corresponds to the desired emission characteristic, to release the light-guiding fiber (112) for use, and if the actual emission characteristic does not correspond to the desired emission characteristic, to output an error message.

9. A method for calibrating a light source (104) of a medical device (102), wherein the light source (104) is connectable to at least one light-guiding fiber (112) such that electromagnetic radiation of a defined light power that is generated by the light source (104) is at least partly coupled into the light-guiding fiber (112), wherein the medical device (102) is connected to at least one calibration port (108), wherein the calibration port (108) comprises sensor means for determining a spatial emission characteristic of a light-guiding fiber (112) introduced into the calibration port (108), wherein the sensor means comprise at least one lateral photodiode (114) arranged laterally at the calibration port (108), and also at least one frontal photodiode (114) arranged at a longitudinal end of the calibration port (108), wherein the method comprises the following steps:

a) connecting the light-guiding fiber (112) to the light source (104), b) inserting a positioning device (110) for the light-guiding fiber (112) into the calibration port (108), wherein the positioning device (110) comprises a receiving channel for receiving the light-guiding fiber (112) and also at least one emission opening, wherein the at least one emission opening enables the transmission of a light power coupled out of the light-guiding fiber (112) in at least one defined spatial direction, c) introducing the light-guiding fiber (112) into the receiving channel of the positioning device (110), d) coupling electromagnetic radiation of a defined light power into the light-guiding fiber (112), e) determining the spatial emission characteristic of the light power coupled out of the light-guiding fiber (112) in the region of the calibration port (108) as an actual emission characteristic, wherein determining the actual emission characteristic comprises determining the respective photocurrent generated in the photodiodes (114) by the light power coupled out from the light-guiding fiber (112), f) determining a desired emission characteristic of the light power coupled out of the light-guiding fiber (112) in the region of the calibration port (108) for the light power coupled into the light-guiding fiber (112) by means of the sensor means, g) comparing the determined actual emission characteristic with the determined desired emission characteristic, wherein comparing the determined actual emission characteristic with the determined desired emission characteristic comprises comparing the determined photocurrents with photocurrents contained in the desired emission characteristic for the respective photodiodes (114), h) if the actual emission characteristic corresponds to the desired emission characteristic, releasing the light-guiding fiber (112) for further use, and i) if the actual emission characteristic does not correspond to the desired emission characteristic, outputting an error message.

10. The method as claimed in claim 9, wherein if the ratios of the photocurrents of the actual emission characteristic correspond to the ratios of the photocurrents of the desired emission characteristic, but the photocurrents of the actual emission characteristic are lower than the corresponding photocurrents of the desired emission characteristic, the error message indicates a defect of the light-guiding fiber (112) and/or of the coupling between the light-guiding fiber (112) and the light source (104) and/or a defective emissive area of the light-guiding fiber (112).

11. The method as claimed in claim 9, wherein after the step of releasing the light-guiding fiber (112), the light source (104) connected to the fiber (112) couples light having a wavelength of between 350 nm and 850 nm into the fiber (112) for a defined time period.

12. A method for calibrating a light source (104) of a medical device (102), wherein the light source (104) is connectable to at least one light-guiding fiber (112) such that electromagnetic radiation of a defined light power that is generated by the light source (104) is at least partly coupled into the light-guiding fiber (112), wherein the medical device (102) is connected to at least one calibration port (108), wherein the calibration port (108) comprises sensor means for determining a spatial emission characteristic of a light-guiding fiber (112) introduced into the calibration port (108), wherein the medical device (102) comprises at least two light sources (104), which are in each case connectable to a light-guiding fiber (112) such that electromagnetic radiation generated by the light sources (104) is in each case at least partly coupled into the light-guiding fiber (112) connected to a light source (104), wherein the method comprises the following steps:

a) connecting the light-guiding fiber (112) to the light source (104), b) inserting a positioning device (110) for the light-guiding fiber (112) into the calibration port (108), wherein the positioning device (110) comprises a receiving channel for receiving the light-guiding fiber (112) and also at least one emission opening, wherein the at least one emission opening enables the transmission of a light power coupled out of the light-guiding fiber (112) in at least one defined spatial direction, c) introducing the light-guiding fiber (112) into the receiving channel of the positioning device (110), d) coupling electromagnetic radiation of a defined light power into the light-guiding fiber (112), e) determining the spatial emission characteristic of the light power coupled out of the light-guiding fiber (112) in the region of the calibration port (108) as an actual emission characteristic, f) determining a desired emission characteristic of the light power coupled out of the light-guiding fiber (112) in the region of the calibration port (108) for the light power coupled into the light-guiding fiber (112) by means of the sensor means, g) comparing the determined actual emission characteristic with the determined desired emission characteristic, h) if the actual emission characteristic corresponds to the desired emission characteristic, releasing the light-guiding fiber (112) for further use, i) if the actual emission characteristic does not correspond to the desired emission characteristic, outputting an error message, and j) wherein at least method steps a) and c) to i) are carried out individually for the light-guiding fibers (112) connected to the light sources (104).

13. The method as claimed in claim 12, wherein after the step of releasing the light-guiding fiber (112), the light source (104) connected to the fiber (112) couples light having a wavelength of between 350 nm and 850 nm into the fiber (112) for a defined time period.

* * * * *